US012714384B2

(12) United States Patent
Yokosawa et al.

(10) Patent No.: US 12,714,384 B2
(45) Date of Patent: Aug. 25, 2026

(54) IMAGE PROCESSING DEVICE, MRI APPARATUS INCLUDING THE SAME, AND IMAGE PROCESSING METHOD

(71) Applicant: FUJIFILM Healthcare Corporation, Kashiwa (JP)

(72) Inventors: Suguru Yokosawa, Chiba (JP); Atsuro Suzuki, Chiba (JP); Toru Shirai, Chiba (JP)

(73) Assignee: FUJIFILM Corporation, Tokyo (JP)

( * ) Notice: Subject to any disclaimer, the term of this patent is extended or adjusted under 35 U.S.C. 154(b) by 281 days.

(21) Appl. No.: 18/412,221

(22) Filed: Jan. 12, 2024

(65) Prior Publication Data

US 2024/0268778 A1 Aug. 15, 2024

(30) Foreign Application Priority Data

Feb. 13, 2023 (JP) ................................ 2023-020124

(51) Int. Cl.
*A61B 6/00* (2024.01)
*G06T 5/50* (2006.01)
(Continued)

(52) U.S. Cl.
CPC .......... *A61B 6/5258* (2013.01); *A61B 6/5235* (2013.01); *G06T 5/50* (2013.01);
(Continued)

(58) Field of Classification Search
CPC ... A61B 6/5258; A61B 6/5235; A61B 5/0033; A61B 5/055; G06T 5/50; G06T 5/70;
(Continued)

(56) References Cited

U.S. PATENT DOCUMENTS

2004/0159812 A1 8/2004 Kaneda et al.
2009/0322863 A1* 12/2009 Takahashi ........ A61B 1/000094 382/106

(Continued)

FOREIGN PATENT DOCUMENTS

| | | | |
|---|---|---|---|
| EP | 1447773 | A2 | 8/2004 |
| JP | 2020-119429 | A | 8/2020 |
| WO | WO2009/128213 | A | 10/2009 |

OTHER PUBLICATIONS

Jul. 17, 2024 European official action in connection with European Patent Application No. 24 15 5871.

*Primary Examiner* — Amara Abdi
(74) *Attorney, Agent, or Firm* — Paul Teng

(57) ABSTRACT

Provided is an image in which noise and artifacts, which pose a problem in intraoperative MRI, are reduced and a decrease in sharpness due to noise reduction for a tissue or a site, for which high visibility is required, is suppressed. In a case of generating and presenting a third MR image by using a first MR image acquired by an MRI apparatus and a second MR image obtained by performing processing of reducing noise and artifacts with respect to the first MR image, a difference for each pixel between the first MR image and the second MR image is taken, and a weighting value for each pixel is calculated using a generated difference image. The weighting value is used to combine the first MR image and the second MR image through weighted averaging for each pixel, and the combined image is presented.

20 Claims, 13 Drawing Sheets

(51) Int. Cl.
*G06T 5/70* (2024.01)
*G06V 10/25* (2022.01)
*G06V 10/56* (2022.01)

(52) U.S. Cl.
CPC ................ *G06T 5/70* (2024.01); *G06V 10/25* (2022.01); *G06V 10/56* (2022.01); *G06T 2207/10088* (2013.01); *G06T 2207/20221* (2013.01); *G06T 2207/20224* (2013.01)

(58) Field of Classification Search
CPC . G06T 2207/10088; G06T 2207/20221; G06T 2207/20224; G06T 2207/20216; G06T 5/60; G06T 11/008; G06V 10/25; G06V 10/56; G01R 33/5608; H04N 23/81; H04N 23/951
See application file for complete search history.

(56) References Cited

U.S. PATENT DOCUMENTS

| | | | | |
|---|---|---|---|---|
| 2013/0216117 | A1* | 8/2013 | Mercuriev | G06T 5/70 382/132 |
| 2014/0211034 | A1 | 7/2014 | Tanaka | |
| 2019/0137589 | A1* | 5/2019 | Noguchi | G01R 33/5608 |
| 2019/0378270 | A1 | 12/2019 | Ida et al. | |
| 2020/0098149 | A1* | 3/2020 | Takemoto | G06T 7/11 |
| 2020/0202486 | A1* | 6/2020 | Nakamura | G06T 7/0016 |
| 2021/0183062 | A1* | 6/2021 | Fukuda | A61B 6/481 |
| 2022/0260659 | A1 | 8/2022 | Shinoda et al. | |
| 2023/0145672 | A1* | 5/2023 | Price | G06T 5/50 348/208.2 |
| 2023/0326099 | A1* | 10/2023 | Lee | G06T 12/30 382/131 |

* cited by examiner 30
20
201
202
203
204
205
213
214
212
215
SEQUENCER
220
COMPUTER
10
IMAGE PROCESSING DEVICE
THIRD IMAGE GENERATION UNIT
DISPLAY CONTROLLER

WEIGHT CALCULATION SECTION

1141

NOISE PATTERN

DB

1142

DIFFERENCE IMAGE

WEIGHTING VALUE FOR EACH PIXEL

IMAGE PROCESSING DEVICE, MRI APPARATUS INCLUDING THE SAME, AND IMAGE PROCESSING METHOD

CROSS-REFERENCE TO RELATED APPLICATION

The present application claims priority from Japanese patent application JP-2023-020124 filed on Feb. 13, 2023, the content of which is hereby incorporated by reference into this application.

BACKGROUND OF THE INVENTION

1. Field of the Invention

The present invention relates to a technique for processing an image acquired by an MRI (magnetic resonance imaging) apparatus, and particularly, to an image processing technique for appropriately processing noise and artifacts according to how the noise or the artifacts occur and presenting the processed image.

2. Description of the Related Art

In recent years, intraoperative imaging, which allows for imaging using an image diagnostic apparatus during surgery and progressing with the surgery appropriately while checking a resection site or the like, has become widespread. An MRI apparatus is also utilized as a means of intraoperative imaging. For example, by repeatedly conducting MRI imaging during surgery and proceeding with the surgery while checking the tumor, it is expected to prevent a tumor from being left behind while preserving a normal tissue.

The MRI apparatus induces nuclear magnetic resonance in the atomic nuclei (usually protons) within tissues constituting a subject and then uses the resulting nuclear magnetic resonance signals to form an image of the subject. The nuclear magnetic resonance signal, which is a high-frequency signal at a predetermined frequency, is susceptible to an influence of radio wave noise emitted from various devices present in an examination room, which poses a problem of noise occurring in the image.

Usually, the MRI apparatus is installed in a shielded room, which blocks external radio wave noise, to suppress the influence of the external radio wave noise. However, in the intraoperative MRI, the MRI apparatus is installed not in the shielded room but in an open-space operating room. Basically, a device that is a source of noise is operated in a manner that power is turned off before conducting MRI imaging. However, due to factors such as forgetting to turn off the power or the introduction of unforeseen devices, it is currently not possible to completely prevent the occurrence of noise. Therefore, in a case where noise has occurred in the image, the basic operation is to use the image as it is in a case where the tumor is visible, and to perform re-imaging in a case where the noise is severe and the tumor is difficult to discern. Since re-imaging leads to an extension in surgical time, noise suppression in the intraoperative MRI has become a significant problem.

In MRI, various techniques for suppressing noise and artifacts occurring in images have been put into practical use, and various methods for solving side effects associated with denoising have also been proposed. For example, in WO2009/128213A, it is proposed that a noise-removed image and a signal-enhanced image are created from a captured image, and these are weighted and combined, in order to remove noise while suppressing edge blurring associated with the noise removal. In addition, in JP2020-119429A, it is proposed that an optimal value of denoising strength is determined based on a plurality of denoised images created with varying levels of the denoising strength, and a difference image between the plurality of denoised images and an original image, thereby improving denoising accuracy. Further, some techniques for applying CNN (convolutional neural network) or the like that have learned various noise patterns to noise removal have also been proposed.

SUMMARY OF THE INVENTION

The above-described related arts all relate to noise suppression processing for the entire image. Meanwhile, occurrence causes of the noise and artifacts that pose particular problems in intraoperative MRI are characterized by their potential, occasional occurrence, or the unpredictability of their timing, such as when devices that should have been turned off are turned on. Therefore, it is difficult to appropriately address these noise and artifacts in the related arts, and it is not possible to solve problems such as reduced visibility of a site of interest even in a case where noise suppression for the entire image is achieved.

An object of the present invention is to solve these problems and to present an image in which noise is effectively suppressed only at a location where noise occurs while preserving an original image as much as possible in a portion where potential or sudden noise does not occur.

In order to solve the above-described problems, according to the present invention, a weighting value in a case of using a difference between an original image, which is acquired by an MRI apparatus, and an image, which is obtained by performing general noise reduction processing on the original image, to perform weighted addition of both the images is decided on for each pixel, and both the images are combined.

That is, according to an aspect of the present invention, there is provided an image processing device that generates and presents a third MR image by using a first MR image acquired by an MRI apparatus and a second MR image obtained by performing processing of reducing noise and artifacts with respect to the first MR image, the image processing device comprising one or more processors which includes: a difference image generation section that takes a difference for each pixel between the first MR image and the second MR image and generates a difference image; a weight calculation section that calculates a weighting value for each pixel by using the difference image; and a composite image generation section that uses the weighting value to combine the first MR image and the second MR image through weighted averaging for each pixel.

In addition, according to another aspect of the present invention, there is provided an MRI apparatus comprising a function of the image processing device of the aspect of the present invention as a function of an image processing unit.

Further, according to still another aspect of the present invention, there is provided an image processing method of generating and presenting a third MR image by using a first MR image acquired by an MRI apparatus and a second MR image obtained by performing processing of reducing noise and artifacts with respect to the first MR image, the image processing method comprising: taking a difference for each pixel between the first MR image and the second MR image and generating a difference image; calculating a weighting value for each pixel by using the difference image; and using the weighting value to combine the first MR image and the second MR image through weighted averaging for each pixel.

It should be noted that, in the present invention, a target of image processing includes noise and artifacts caused by various causes, but these are collectively referred to simply as noise in the present specification. Similarly, a region where noise and artifacts have occurred on an image is simply referred to as a noise occurrence region.

According to the aspects of the present invention, in a case where an original image and an image processed by general noise reduction processing are combined through weighted addition, use of a weight corresponding to a degree of noise occurrence, which is calculated for each pixel, makes it possible to obtain an image in which an influence of potential noise, unexpectedly occurring noise, or the like is eliminated without compromising information of the original image. As a result, in intraoperative MRI or the like, side effects such as reduced visibility of an issue, which is a target of surgery, or a surrounding tissue can be minimized, and a probability of re-imaging or extensions in surgical time associated with the re-imaging can be reduced.

BRIEF DESCRIPTION OF THE DRAWINGS

FIG. 12 is a diagram showing an example of a weight calculation section of Embodiment 3.

DESCRIPTION OF THE PREFERRED EMBODIMENTS

Hereinafter, embodiments of an image processing device and an image processing method according to the present invention will be described with reference to the drawings.

Figure 1:
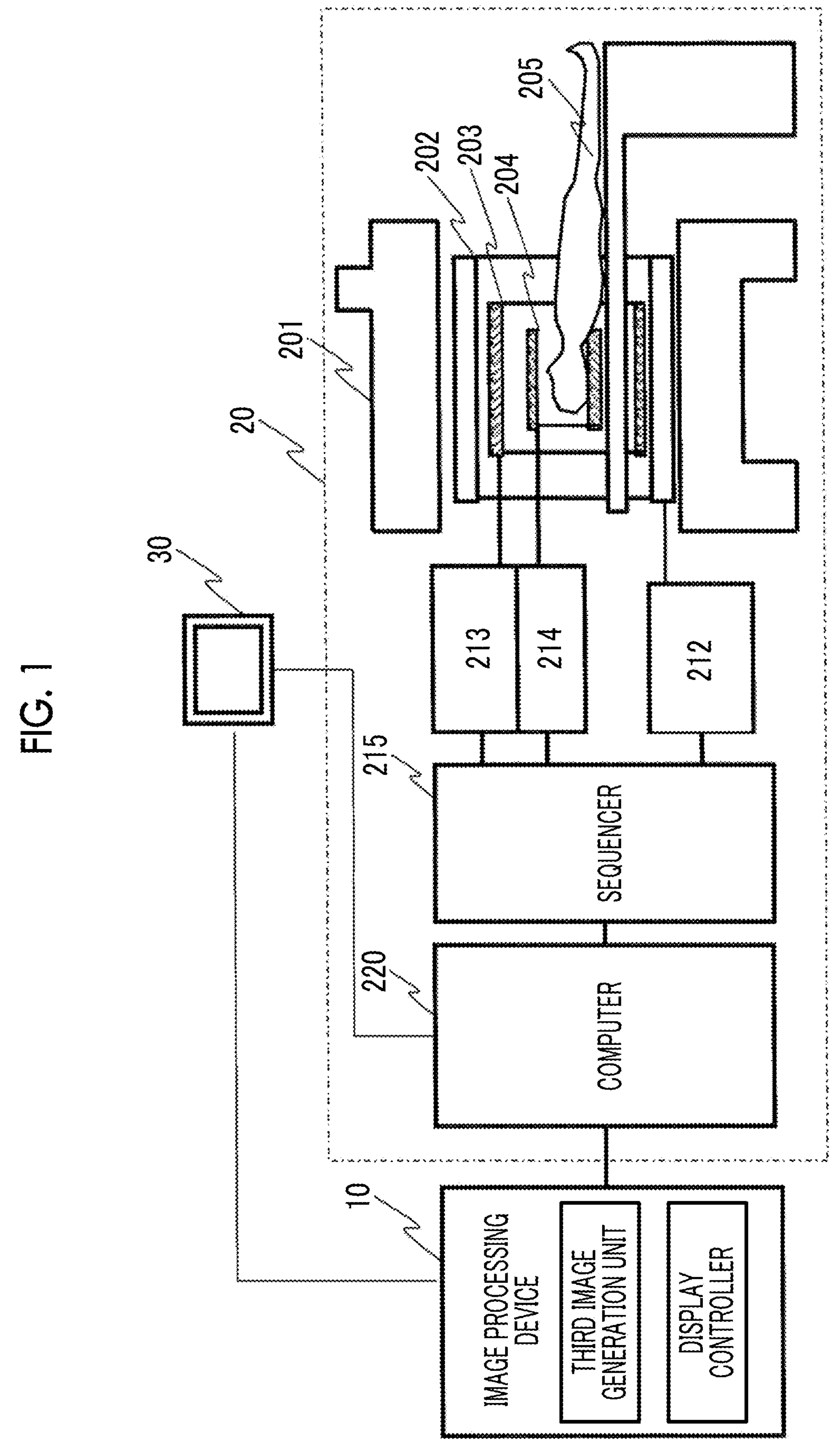
FIG. 1 is a diagram showing an outline of an examination system including an MRI apparatus and an image processing device.

The image processing device of the embodiment of the present invention is an image processing device that is used to process an MR image acquired by an MRI apparatus to present the processed image to a doctor, an imaging technician, or the like who is performing an MR examination (hereinafter, collectively referred to as a user) as an image useful for diagnosis, and is configured to present the image after processing to, for example, a display device 30 placed in an examination room (shielded room) in which an MRI apparatus 20 is installed, as shown in FIG. 1. An image processing device 10 itself may be placed in a separate operation room or at a remote location from the examination room, may be located in the same examination room as the MRI apparatus 20, or may be an accessory device of the MRI apparatus itself.

The MRI apparatus 20 is the same as a general MRI apparatus, and comprises a static magnetic field generation magnet 201 that generates a static magnetic field in a space (examination space) in which a subject 205 is placed, for example, a superconducting magnet, a normal conducting magnet, a permanent magnet, or the like, a gradient magnetic field coil 202 that is disposed in a static magnetic field space generated by the static magnetic field generation magnet 201, high-frequency coils (a transmission RF coil 203 and a reception RF coil 204), a gradient magnetic field power supply 212 and a transmitter 213 that drive the gradient magnetic field coil 202 and the high-frequency coil 203, a receiver 214 that receives a nuclear magnetic resonance signal detected by the reception RF coil 204, and a sequencer 215 that operates the gradient magnetic field power supply 212, the transmitter 213, and the receiver 214 in accordance with a predetermined pulse sequence.

Further, the MRI apparatus 20 comprises a computer 220 that controls operations of the transmitter 213, the gradient magnetic field power supply 212, and the receiver 214 via the sequencer 215 and that processes the nuclear magnetic resonance signal received by the receiver 214 to perform computational operations (image processing) such as image reconstruction of an examination target. The image processing performed by the computer 220 may include, in addition to image reconstruction using general Fourier transformation and sequential reconstruction, known noise reduction processing on the reconstructed image, and the like.

In addition, the display device 30 that displays a reconstructed image, an input device and an external storage device (not shown), and the like are connected to the computer 220, and the user can send instructions necessary for the operation of the MRI apparatus 20 or transmit images to the external storage device, via the display device and the input device. The display device 30 provided in the MRI apparatus 20 can also function as a display device that displays a processing result of the image processing device 10.

Hereinafter, an outline of the configuration and operation of the image processing device 10 will be described by using a case where the image processing device 10 is provided independently of the computer of the MRI apparatus as an example.

The image processing device 10 can be configured by a general-purpose computer provided with a CPU and a memory, and comprises a third image generation unit 110 that performs processing on an image acquired by the MRI apparatus 20 and that generates an image useful for the user who is operating the MRI apparatus 20, and a display controller 130 that generates an image for presenting the image generated by the third image generation unit 110 and that displays the generated image on the display device 30, as functions related to the present invention. Although not shown in FIG. 1, the image processing device 10 also includes a memory or a storage device that stores various kinds of data used by the third image generation unit 110, image data during calculation, and the like. Further, a function other than the third image generation unit 110 need not be provided, a part of the processing performed by the image processing device 10 may be performed by a programmable IC such as ASIC, and the image processing device 10 may include an AI function such as CNN that has been trained on the computer inside or outside of the image processing device 10.

The third image generation unit 110 uses an original image (first MR image), which is reconstructed by the MRI apparatus 20, and a noise-reduced image (second MR image), which is obtained by performing known noise reduction processing on the first MR image, to generate a third image in which noise is removed, with noise and artifacts occurring during imaging or during surgery performed during imaging as a target, and presents the third image to the user.

With regard to the second MR image, in a case where noise reduction processing is included as image processing performed by the computer 220 of the MRI apparatus 20, the image processed by the computer 220 may be used as the second MR image, or the image processing device 10 may import the original image from the MRI apparatus 20 and perform known noise reduction processing.

Figure 2:
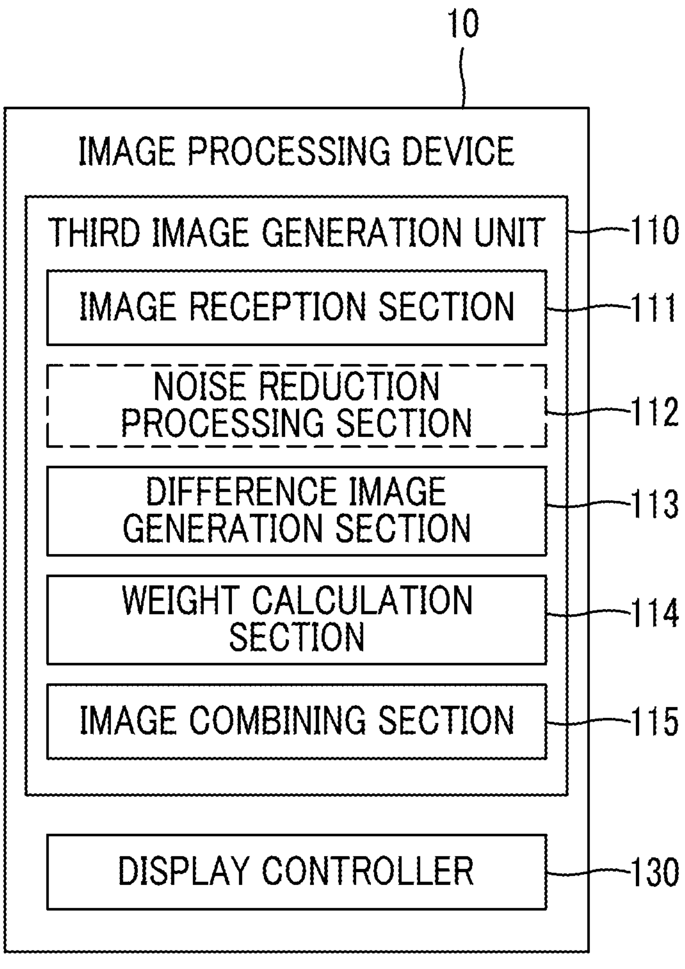
FIG. 2 is a functional block diagram of the image processing device according to Embodiment 1 of the present invention.

FIG. 2 shows a functional block diagram of the third image generation unit 110. As shown in the figure, the third image generation unit 110 comprises an image reception section 111 that receives an image from the MRI apparatus 20, a noise reduction processing section 112, a difference image generation section 113 that generates a difference image between the first MR image and the second MR image, a weight calculation section 114 that uses a pixel value of each pixel in the difference image to calculate a weighting value for each pixel, and an image combining section 115 that uses the weighting value calculated by the weight calculation section 114 to combine the images. A dashed rectangle indicating the noise reduction processing section 112 means that this function may be either a function of the image processing device 10 or a function of the MRI apparatus, as described above.

Figure 3:
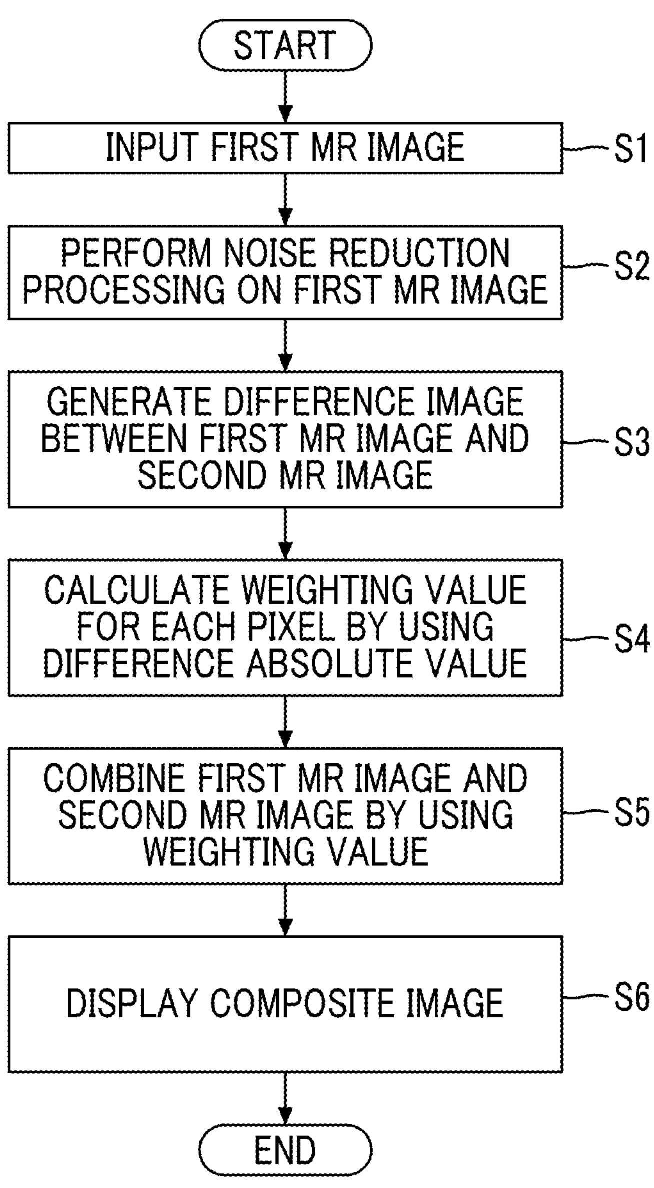
FIG. 3 is a diagram showing a flow of processing of the image processing device of Embodiment 1.

FIG. 3 shows a flow of the operation of the third image generation unit 110 configured as described above. Here, it is assumed that intraoperative MRI is performed.

First, in a case where an image (first MR image) reconstructed by the MRI apparatus 20 is input by the image reception section 111 (S1), the noise reduction processing section 112 performs noise reduction processing on the first MR image (S2). The noise reduction processing performed here is not particularly limited as long as it is generally known processing, and for example, any of processing of removing artifacts characteristically occurring depending on an imaging method through computational operations, processing using a filter, processing using CNN that has learned a noise image and a noise-free image as learning data, or the like can be employed, and a plurality of the processing may also be combined as necessary. Further, in the noise reduction processing using the filter, the filtering strength may be adjusted according to the noise, and the sharpness of the image after noise reduction may be adjusted. Through the processing by the noise reduction processing section 112, an image (second MR image) in which noise is reduced throughout the entire image can be obtained.

Next, the difference image generation section 113 takes a difference between the original image before the noise reduction and the second MR image after the noise reduction processing to generate a difference image and to calculate an absolute value of the difference of each pixel (S3).

The weight calculation section 114 calculates a weighting value for each pixel by using the absolute value of the difference of each pixel calculated by the difference image generation section 113 (S4). The image combining section 115 combines the original image and the noise-reduced image for each pixel by using the weighting value for each pixel to generate a composite image which is the third image (S5). The processing of the third image generation unit 110 is completed with the above S1 to S5.

The display controller 130 causes the display device 30 to display the third image generated by the third image generation unit 110 (S6). The form of the display is not particularly limited and will be described in detail in the embodiment to be described below. However, in order to make it easier for the user to check a region where processing is performed with respect to the original image, particularly a region with a high degree of noise reduction processing, it is preferable to display two images in parallel or superimposed. In a case of superimposing the two images, color coding or the like is performed to enhance visibility.

According to the present embodiment, the magnitude of the difference (absolute value) between the original image and the image after noise reduction is obtained for each pixel, and a weight for each pixel is set based on the magnitude of the difference to combine the images, whereby it is possible to present a third MR image in which noise reduction focused on noise that interferes with the checking of the original image is performed while preserving the maximum amount of information from the original image, such as, for a region where significant noise has occurred, that is, a region where the difference is large, increasing the weight of the noise-reduced image in the region and decreasing the weight of the original image, or for a region where little or no noise has occurred, increasing the weight of the original image in the region. As a result, it is possible to appropriately suppress the influence of noise that occurs temporarily and spatially in a limited manner due to operations of unforeseen devices during surgery, or the like and there is no risk that sites such as a critical site, which is a target of the surgery, are blurred by noise reduction throughout the entire image, which makes it possible to provide a useful intraoperative image.

Although the outline of the image processing device 10 of the embodiment of the present invention has been described above, the details of the processing performed by the image processing device 10 will be further described in the following embodiments.

Embodiment 1: Embodiment of Method

In the present embodiment, the weight calculation section 114 of the third image generation unit 110 calculates a weight coefficient $\alpha$ for each pixel by using the absolute value of the difference of each pixel calculated by the difference image generation section 113 and calculates a weighting value using the weight coefficient $\alpha$ as an exponent, as the weighting value.

Since the flow of processing is the same as that of FIG. 3, the processing of the present embodiment will be described below with reference to FIG. 3.

Figure 4:
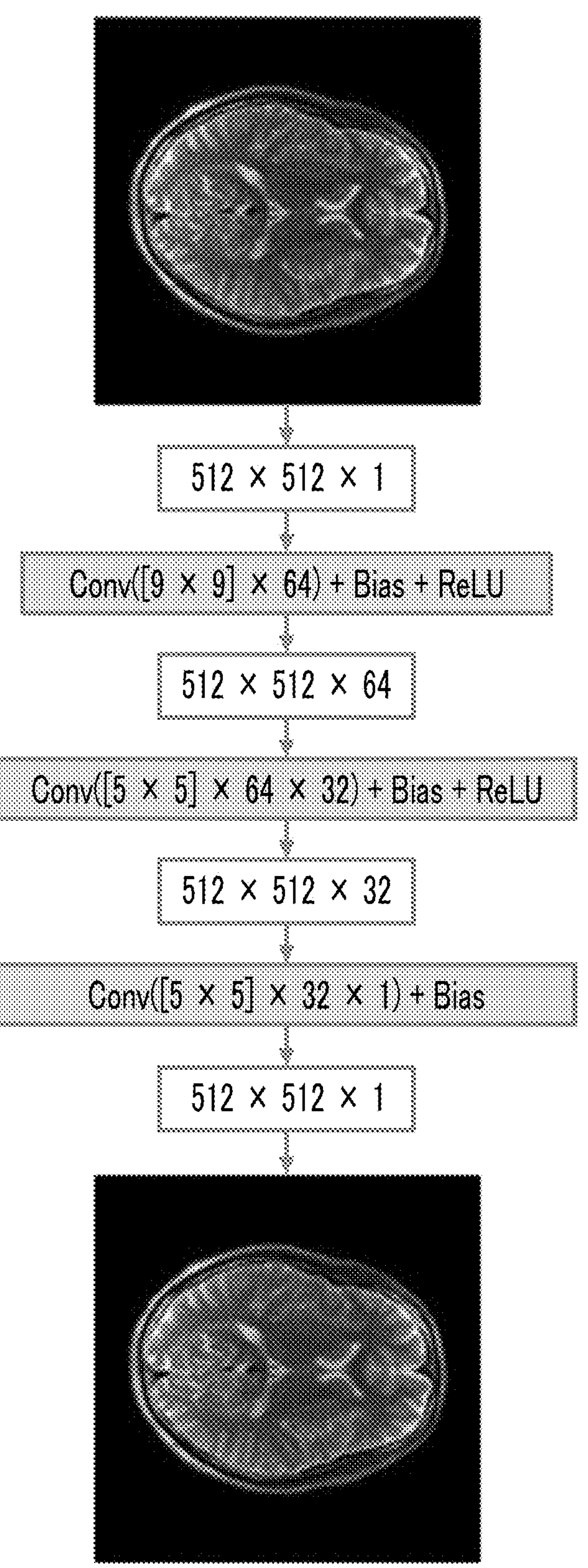
FIG. 4 is a diagram showing one embodiment of a noise reduction section.

First, the noise reduction processing section 112 performs noise reduction processing on the original image (first MR image) acquired by the MRI apparatus 20 and generates the second MR image (S1, S2). Here, as an example, noise removal is performed using a super resolution convolutional neural network (SRCNN) of all three layers as shown in FIG. 4. This CNN is designed to remove random noise by using a random noise pattern as learning data, and the image after noise reduction (second MR image) tends to become blurred, which causes brain sulci or tumor boundaries to become indistinct, but the influence of the image processing cannot be grasped.

The third image generation unit 110 combines the original image and the CNN-processed image to obtain the combined third image. In that case, a composite image in which information that has been compromised by the noise reduction processing is reproduced as faithfully as possible is generated such that the combined image tends to lean toward the image after CNN processing for a location where local noise or artifacts have occurred, while the combined image leans toward the original image for the other positions.

Therefore, first, the difference image generation section 113 calculates an absolute value d of the difference in signal intensity for each pixel between the original image and the image after CNN processing by using Equation (1) (S3).

$$d(i, j) = |I_{CNN}(i, j) - I_{org}(i, j)| \tag{1}$$

In Equation (1), $I_{CNN}$ represents the image after CNN processing, $I_{org}$ represents the original image, and (i,j) represents a pixel position (hereinafter, the same).

The difference in signal intensity, which is denoted by d, is large in a position where local noise or artifacts have occurred, but is small in the other region.

The weight calculation section 114 calculates the coefficient $\alpha$ (referred to as a weight coefficient) in which the absolute value d of the difference is standardized by the average value of d by using Equation (2). The weight coefficient $\alpha$ is obtained for each pixel and is used to decide on the weighting value. In the present embodiment, a weight of an image in a case of performing weighted addition of the original image and the image after CNN processing is used as a fixed value (fixed weight), and the weight coefficient $\alpha$ is used as an exponent of the fixed weight. Therefore, a lower limit value and an upper limit value are set in advance for a. As an example, it is assumed that the lower limit value is 0.01 and the upper limit value is 100.

$$\alpha(i, j) = \frac{\bar{d}}{d(i, j)} \tag{2}$$

Next, the weight calculation section 114 decides on a weighting value $W^{\alpha}$ in the image weighted addition represented by Equation (3) (S4), and the image combining section 115 uses Equation (3) to generate an image (third image) in which a degree of noise processing is adjusted according to a noise occurrence position.

$$I_{adj}(i, j) = (I_{CNN}(i, j) - I_{org}(i, j)) \cdot W^{\alpha(i,j)} + I_{org}(i, j) \tag{3}$$

Here, $I_{adj}$ represents an image after adjustment, and W represents the fixed weight. The fixed weight takes a value in a range of 0 to 1, and an appropriate value is set in advance as the weight in a case of combining the image after CNN processing and the original image separately from the adjustment in the present embodiment. Specifically, as the fixed weight W, an appropriate weight for obtaining an image in which random noise is suppressed while preserving the information of the original image can be determined to either be set as a default or be user-settable according to a noise pattern included in the original image, a method for processing of reducing noise and artifacts such as CNN processing, or the like.

Figure 5:
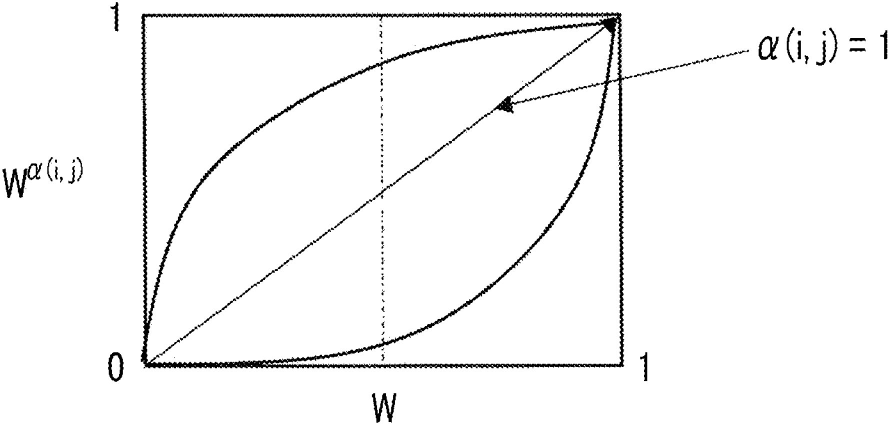
FIG. 5 is a diagram illustrating a weighting value.
Figure 5:
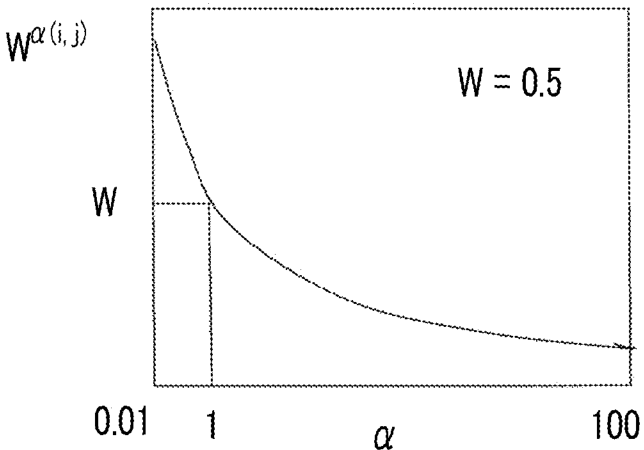

A relationship between such a fixed weight W and the weighting value $W^{\alpha}$ using the weight coefficient for each pixel as an exponent is schematically shown on the upper side of FIG. 5. As shown in a graph on the upper side of FIG. 5, in a case where a, which is an indicator of the pixel signal intensity difference, satisfies $\alpha$=1 (a straight line), $W^{\alpha}$ takes the same value as W, but exponentially changes based on the value of $\alpha$. A graph on the lower side of FIG. 5 shows a case where W=0.5 as an example, and as shown in this graph, in a case where a is smaller than 1, the weighting value $W^{\alpha}$ takes a value greater than W, which results in a larger weight for the CNN-processed image. That is, the weighting value for the noise occurrence position where the absolute value of the difference is large (the weight coefficient $\alpha$ is small) is decided on to be large.

In Equation (3), although the weight coefficient is used as the exponent of the fixed weight W, the method of deciding on the weighting value using the weight coefficient $\alpha$ for each pixel is not limited to Equations (2) and (3), and for example, a method of setting a weight coefficient standardized by the maximum value of d to $\alpha'$ and using a weighting value $W\alpha'$ can also be employed.

After the weighting value is determined in this way, the image combining section 115 performs the weighted addition of the original image and the CNN-processed image in accordance with Equation (3) to generate a composite image which is the third image (S5). In the composite image, in a case where the fixed weight is used as a reference, in pixels in which noise has occurred and the signal intensity difference is large, the CNN-processed image has a larger weight, but in pixels in which no noise has occurred, the original image has a larger weight, which results in an image that reflects more information of the original image.

Figure 6:
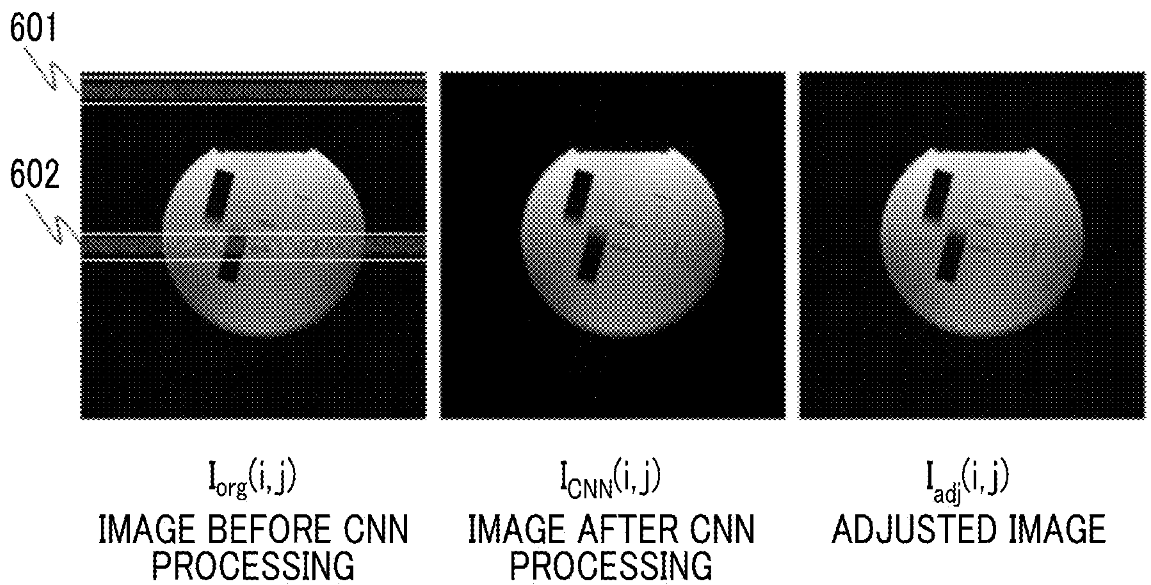
FIG. 6 is a diagram illustrating processing of the embodiment of the present invention.

FIG. 6 shows an example of an image generated through the image processing of the present embodiment. In the figure, the left side is the original image (image before CNN processing), the center is the image after noise reduction processing (image after CNN processing), and the right side is a composite image (adjusted image).

The original image has noise occurring in regions 601 and 602 surrounded by rectangles in the figure, and the noise disappears in the image after CNN processing by performing the noise reduction processing on this image, but the overall sharpness has decreased, which results in a slight blurring of brain sulci, bleeding parts, or the like. In the adjusted image obtained by combining these two images with an appropriate weight for each pixel using the method of the present embodiment, noise is reduced in the noise occurrence region, and sharpness close to that of the original image is obtained in the other region.

In a case of intraoperative MRI, the image (adjusted image) combined by the image combining section 115 is immediately displayed on the display device 30 disposed close to the imaging unit of the MRI apparatus. Therefore, the display controller 130 receives the composite image from the image combining section 115 and generates a display image. The display image may be only the adjusted image as shown on the right side of FIG. 6, but in order to make it easier for the user to check the adjusted region, the original image and the image after CNN processing may be displayed together, or the difference image may be displayed. As one aspect of displaying the difference image, for example, the adjusted image may be displayed in one color such as black and white, and the difference image may be superimposed and displayed on the adjusted image in a color different from that of the adjusted image. In this case, it is preferable to make the display of the difference image transparent to maintain the visibility of the adjusted image. In addition, the display of the difference image may be made user-selectable between being displayed and hidden.

This enables the user to proceed with the surgery while checking and reading reliable image information.

According to the present embodiment, it is possible to provide an image in which the influence of noise is reduced while ensuring the sharpness of the tissue that the user wants to observe even in a case where noise has occurred in an image due to potential noise or sudden radio wave noise.

Embodiment 2: Embodiment of Region Specification

Figure 7:
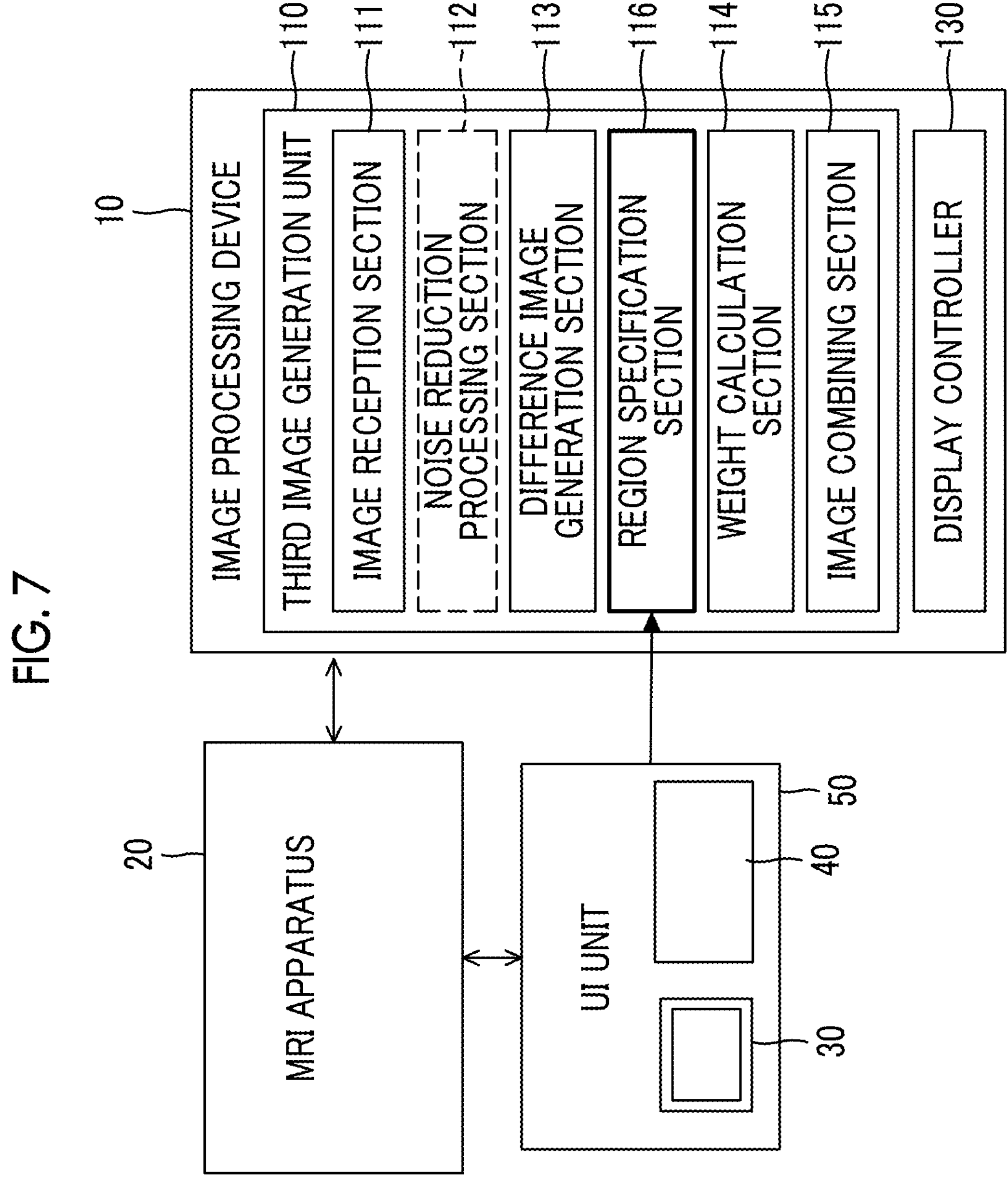
FIG. 7 is a functional block diagram of an image processing device of Embodiment 2.

In Embodiment 1, the weight is decided on by determining whether or not noise has occurred from the signal intensity difference for each pixel. However, the present embodiment is characterized by specifying a region where noise has occurred based on the signal intensity difference for each pixel and varying weighting rules between the specified region and the other region. The "noise occurrence region" in the present embodiment includes not only a region in an image space but also a region in a data space representing the magnitude of the difference. Therefore, in the image processing device of the present embodiment, as shown in the functional block diagram of FIG. 7, the third image generation unit 110 comprises a region specification section 116. In the embodiment shown in FIG. 7, the region specification section 116 receives a user designation through the UI unit 50 provided with the display device 30 and the input device 40, which are attached to the MRI apparatus 20, and specifies the region. In FIG. 7, the same elements as those in FIG. 2 are designated by the same reference numerals, and the overlapping description will not be repeated.

Hereinafter, processing by the image processing device of the present embodiment will be described with reference to FIG. 8, with a focus on the differences from Embodiment 1.

First, in the same manner as in Embodiment 1, the original image reconstructed by the MRI apparatus 20 is input, the noise reduction processing is performed on the original image, and the difference for each pixel between the original image and the noise-reduced image is calculated (S1 to S3). The display controller 130 displays the difference image obtained using the difference for each pixel or the original image on the display device 30 of the UI unit 50 (S31).

The user looks at the image displayed on the display device 30 and designates a region where noise or artifacts have occurred. For example, in a case where the original image as shown on the left side of FIG. 6 is displayed, the regions 601 and 602 determined by the user to be noise occurrence regions are selected and designated through the input device 40 such as a pointer or a mouse. The region specification section 116 receives the user designation (S32) and specifies the noise occurrence (the region of the image space) region. Similarly, in a case where the difference image is displayed, the noise occurrence region can be specified by the user through the designation of a region with high signal intensity in the difference image via the UI unit 50.

Figure 8:
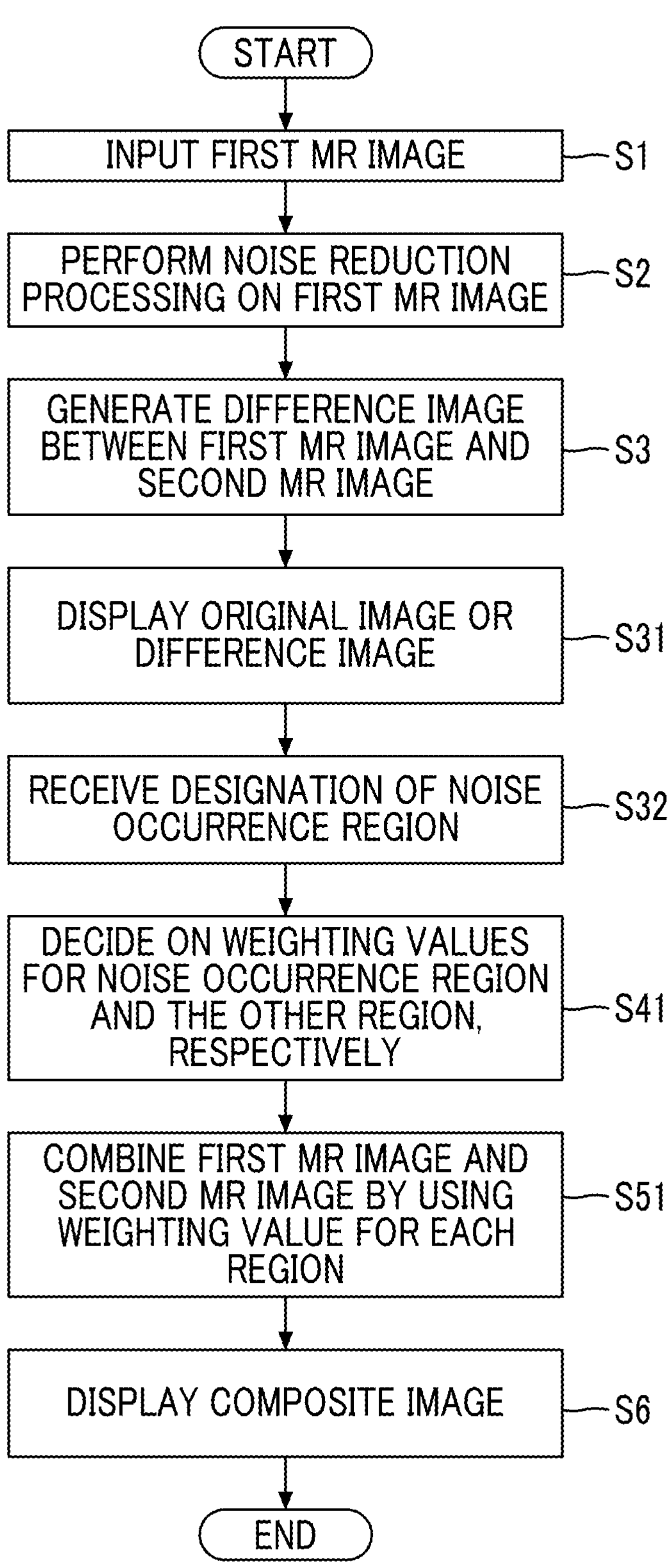
FIG. 8 is a diagram showing an example of a flow of processing of the image processing device of Embodiment 2.
Figure 9:
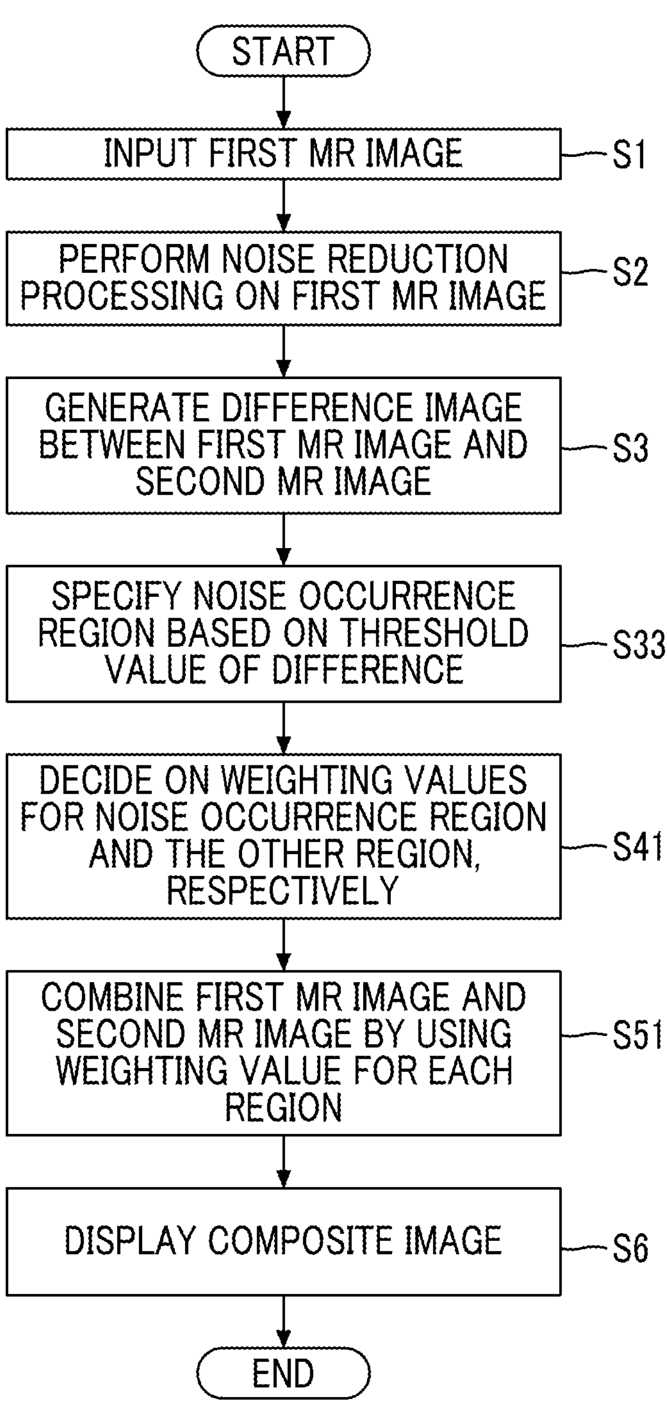
FIG. 9 is a diagram showing another example of the flow of the processing of the image processing device of Embodiment 2.
Figure 10:
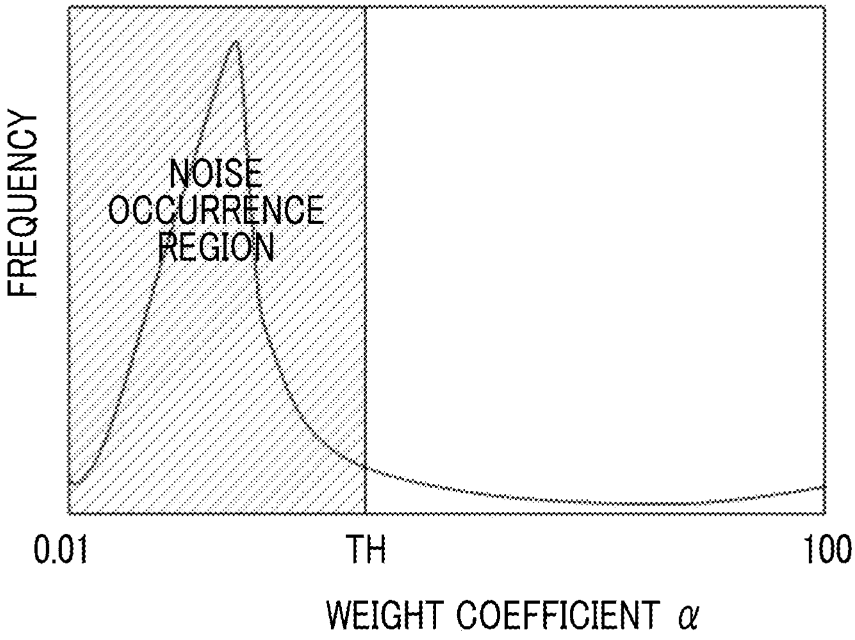
FIG. 10 is a diagram illustrating region specification in a data space.

Further, as shown in FIG. 9, a predetermined threshold value is set in advance for the weight coefficient $\alpha$ using the absolute value of the difference or Equation (2) mentioned above, and the region specification section 116 may specify a position where the weight coefficient $\alpha$ is equal to or less than the threshold value, that is, the absolute value of the difference increases, as the noise occurrence region (S33). In this case, steps S31 and S32 of FIG. 8 can be omitted. For example, in a histogram of the weight coefficient $\alpha$ as shown in FIG. 10, a region (a region on the data space) 603 having a threshold value TH or less is set as the noise occurrence region. The threshold value can be determined by using a discriminant analysis method or the like. Alternatively, the threshold value may be set in advance, but GUI that receives a numerical value input or an input by the operation on the histogram may be displayed on the display device 30 of the UI unit 50. This makes it possible to specify the noise region based on the user's perception.

In addition, in the specification of the noise occurrence region, a method using the user designation (FIG. 8) and a method using the threshold value (FIG. 9) have been described, but any one of these methods may be employed, or both of them can also be employed. In that case, the region specification section 116 takes AND or OR on the regions designated by the two methods to specify the noise occurrence region.

After the noise region is specified, the weight calculation section 114 decides on the weighting values for the noise occurrence region and the other region in accordance with different weighting rules (S41), respectively.

An example of the method of varying weighting rules is, as shown in FIG. 8, to vary the fixed weight W used in Equation (3) between the noise occurrence region and the other region. For example, the noise occurrence region is set to have a larger fixed weight than the other region. The calculation of the actually applied weighting value $W^{\alpha}$ as a function of the weight coefficient $\alpha$ for each pixel is the same as that of Embodiment 1. However, due to the difference in the fixed weights W, in the noise occurrence region, the weighting value is greater than in the other region, and the combined image closely resembles the noise reduction processed image in the noise occurrence region.

As the method of varying the weighting rules, a weighting value based on the weight coefficient may be calculated only for the noise occurrence region, and the weighting value=the fixed weight W may be set for the other region. In this case, after the noise occurrence region is specified through the user designation, the weight coefficient need only be calculated only for that region, so that the computational load can be reduced and the time required for the presentation of the composite image can be accelerated.

For each region, obtaining the composite image through the weighted addition (S51) after calculating the weighting value, and displaying the composite image (S6) are the same as in Embodiment 1. The aspect of display can also be made the same as the aspect described in Embodiment 1. However, in a case where the threshold value of the difference between images is set at the time of region specification or in a case where the threshold value of the difference is set by the user when superimposing and displaying the difference image on the original image in a different color, the color need not be displayed for a region where the difference is lower than the threshold value. As a result, it is possible to present only the information on the region or the position that the user wants to check without presenting redundant information. In addition, in a case where two or more regions are specified by the region specification section 116, each region may be displayed with a different color. For example, a predetermined range designated by the user, a dot-like noise position selected by using the threshold value, and the like are displayed in different colors. This makes it possible to check the difference in the pattern or in the occurrence position of the noise having different occurrence causes.

Embodiment 3

In the present embodiment, image adjustment corresponding to the noise or artifact pattern is performed (the first MR image and the second MR image are combined). The functional block diagram of the image processing device of the present embodiment is basically the same as the functional block diagram of Embodiment 1 shown in FIG. 2 or the functional block diagram of Embodiment 2 shown in FIG. 7, and in the following description, reference is made to these drawings. However, the present embodiment is characterized in that the weight calculation section 114 calculates or decides on weighting values corresponding to various noise patterns.

Figure 11:
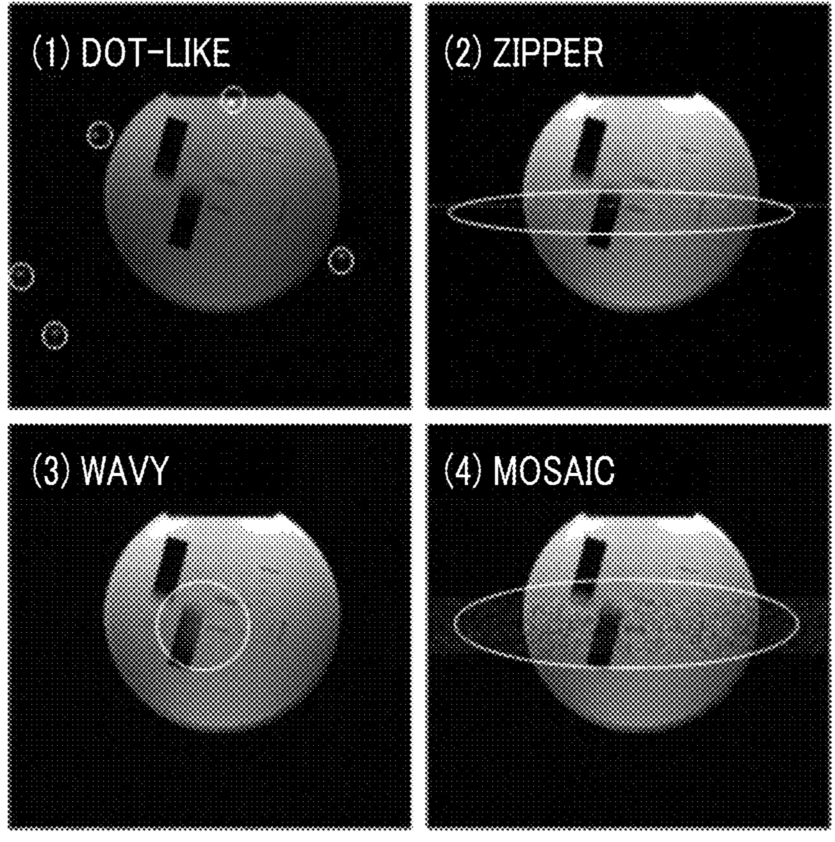
FIG. 11 is a diagram showing an example of a noise pattern.

FIG. 11 shows some patterns of noise occurring in the MR image. In FIG. 11, the upper left shows a dot-like pattern with dot-like noise occurring at unspecified positions, with other patterns representing noise occurring within a limited range, the upper right shows a zipper-like pattern with noise occurring in a dashed line shape, the lower left shows a wavy pattern in which one or a plurality of regions become streaked, and the lower right shows a mosaic-like pattern resulting in a roughened image. In addition, there is a noise pattern peculiar to the MR image. Further, the distribution of noise intensity (the pattern of the histogram) also differs depending on these noise patterns, and appropriate weighting values and fixed weights differ.

The weight calculation section 114 applies a weighting method corresponding to the noise pattern by using a processor, such as machine learning, to decide on the weighting value for each pixel.

As the processor, a known algorithm that has been developed for machine learning can be used. Hereinafter, an example of a method of deciding on the weighting value corresponding to the noise pattern will be described.

Figure 12:
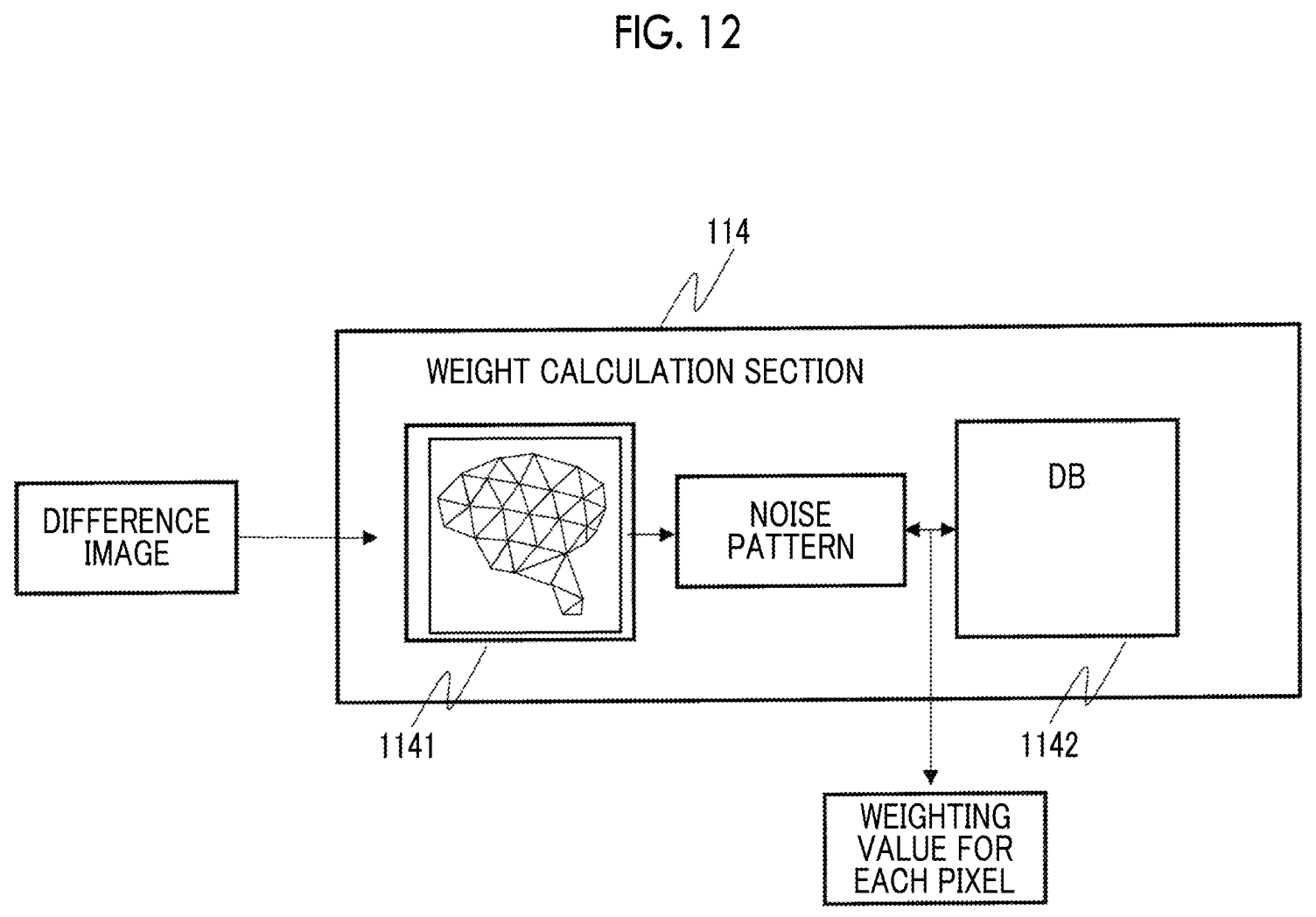

In a first method (Method 1), as shown in FIG. 12, a processor 1141 that receives the difference image as an input and outputs a noise pattern is provided, and various predetermined noise patterns and calculation algorithms for weighting values are stored in a database (DB 1142) in association with each other. The difference image represents a difference in signal intensity for each pixel between the original image and the image after noise reduction processing and includes information such as a magnitude of the signal intensity, a distribution in the image space, an intensity distribution, or the like. The processor is trained in advance using pairs of noise patterns and various difference images having these elements different from each other as training data and is trained to classify the difference images into the noise patterns.

Meanwhile, the relationship between the noise pattern and the calculation algorithm for the weighting value is specifically a calculation expression for calculating the weighting value from the weight coefficient $\alpha$ and the fixed weight W corresponding to the noise pattern. For example, a relational expression is used in which the value of the fixed weight of the image after noise reduction processing is reduced in a case where the noise intensity obtained from the difference image is relatively small, a weighting algorithm that uses the weight coefficient $\alpha$ as the exponent of the fixed weight is used in a case where the noise intensity distribution exponentially changes, and for a pattern with a noise intensity distribution having a peak, heavier weights are set only in pixels near the peak. Although the DB 1142 that stores the relationship between such a noise pattern and the calculation algorithm for the weighting value is provided in the weight calculation section 114 in FIG. 12, the DB 1142 may be provided in the storage device in the image processing device 10 or the external storage device.

In a case where the processor receives the difference image as an input and outputs the noise pattern corresponding to the difference image, the weight calculation section 114 refers to the DB to select a calculation algorithm corresponding to the output noise pattern and calculates the weighting value for each pixel.

Figure 13:
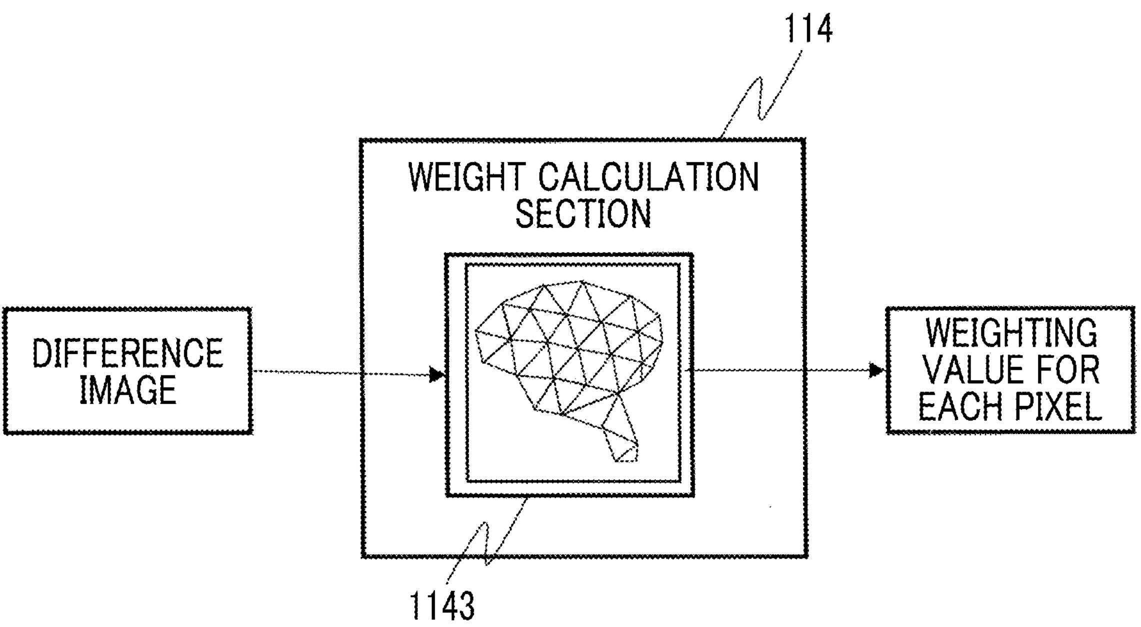
FIG. 13 is a diagram showing another example of the weight calculation section of Embodiment 3.

In a second method (Method 2) using a processor, as shown in FIG. 13, a processor 1143 that receives the difference image created from the difference between the first MR image and the second MR image as an input and outputs the weighting value for each pixel is used. The processor 1143 is configured with, for example, a machine learning algorithm that has learned to output the optimal fixed weight and the relationship between the fixed weight and the weighting value by using, as learning data, various difference images or histograms thereof, the weighting value for each pixel, which is adjusted in advance, or the weighting value to be decided on according to the noise pattern, which is obtained by classifying the noise patterns through Method 1 and storing the noise patterns in the database.

In Method 1, the processor 1141 first classifies the difference image into a noise pattern and then refers to the DB 1142 in which the noise pattern and the calculation algorithm for the weighting value are associated with each other, but in the present method, the processor 1143 receives the difference image as an input and outputs the optimal weighting value without outputting the noise pattern.

In both Methods 1 and 2, combining images by using the weighting value through the image combining section 115 after deciding on the weighting value, and displaying the combined image on the display device 30 are the same as in Embodiment 1 and Embodiment 2, and the form of the display is also the same.

According to the present embodiment, it is possible to decide on the optimal weighting value according to the difference image through the trained CNN or the like, and it is possible to present the adjusted image with high accuracy corresponding to the noise pattern.

EXPLANATION OF REFERENCES

- 10: image processing device
- 110: third image generation unit
- 111: image reception section
- 112: noise reduction processing section
- 113: difference image generation section
- 114: weight calculation section
- 115: image combining section
- 116: region specification section
- 20: MRI apparatus
- 30: display device
- 40: input device
- 50: UI unit

What is claimed is:

1. An image processing device that generates and presents a third MR image by using a first MR image acquired by a magnetic resonance imaging apparatus and a second MR image obtained by performing processing of reducing noise and artifacts with respect to the first MR image, the image processing device comprising one or more processors configured to:

generate a difference image by taking, for each pixel, a difference in signal intensity between the first MR image and the second MR image;

calculate, for each pixel, a corresponding weighting value by using the difference image; and generate the third MR image by using weights including for each pixel the corresponding weighting value to combine the first MR image and the second MR image through weighted averaging for each pixel, the weight value applied for each pixel monotonically increasing as a magnitude of the difference for the pixel in the difference image increases.

2. The image processing device according to claim 1, wherein the one or more processers comprise a noise reduction section that generates the second MR image in which noise and artifacts are reduced with respect to the first MR image.

3. The image processing device according to claim 1, wherein the one or more processers comprise a region specification section that uses the difference image to specify a region where noise and artifacts have occurred in the first MR image.

4. The image processing device according to claim 3, wherein the one or more processers vary a conditional expression used to calculate the weighting value between the region specified by the region specification section and the other region.

5. The image processing device according to claim 3, wherein the one or more processers calculate the weighting value such that a weight of a pixel of the second MR image is greater than a weight of a pixel of the first MR image for the region specified by the region specification section, and a weight of a pixel of the first MR image is greater than a weight of a pixel of the second MR image for a region other than the region specified by the region specification section.

6. The image processing device according to claim 3, wherein the region specification section specifies the region where noise and artifacts have occurred based on a threshold value for a difference of pixel values calculated by the one or more processers.

7. The image processing device according to claim 3, further comprising:

a UI unit that receives a designation of a user, wherein the region specification section specifies a region designated by the user via the UI unit as the region where noise and artifacts have occurred.

8. The image processing device according to claim 1, wherein the one or more processers comprise a display controller that controls an image to be displayed on a display device, and the display controller cause to be displayed on the display device a composite image generated by the one or more processers, and the difference image or a part of the difference image.

9. The image processing device according to claim 8, wherein the display controller cause to be displayed on the display device the composite image in a first color, and superimposes and displays the difference image or the part of the difference image in a second color that is different from the first color.

10. The image processing device according to claim 9, wherein the display controller cause to be displayed on the display device the difference image in a plurality of colors different from the first color according to pixel values.

11. The image processing device according to claim 8, wherein the display controller cause to be displayed on the display device a pixel of the difference image whose pixel value is equal to or greater than a predetermined threshold value.

12. The image processing device according to claim 1, wherein the one or more processers calculate a weight coefficient $\alpha$ with respect to a pixel value by using the difference image and calculates the weighting value for each pixel by using a fixed weight W (W=0 to 1) and the weight coefficient.

13. The image processing device according to claim 12, wherein the one or more processers use the weight coefficient $\alpha$ as an exponent of the fixed weight W to decide on the weighting value for each pixel, which is denoted by $W^{\alpha}$.

14. The image processing device according to claim 12, wherein the one or more processers include a region specification section that uses the difference image to specify a region where noise and artifacts have occurred in the first MR image, and varies the fixed weight W according to the region where noise and artifacts have occurred and the other region.

15. The image processing device according to claim 12, wherein the one or more processers include a processor that receives the difference image as an input and that outputs a weighting value for each pixel corresponding to a noise pattern.

16. The image processing device according to claim 1, wherein the one or more processers include a processor that receives the difference image as an input and that outputs a noise pattern, and calculates the weighting value for each pixel by selecting, based on a correspondence between various predetermined noise patterns and calculation algorithms for weighting values, a calculation algorithm corresponding to the noise pattern output by the processor.

17. A magnetic resonance imaging apparatus comprising:

an imaging unit that collects a nuclear magnetic resonance signal generated by a subject and reconstructs an image of the subject by using the nuclear magnetic resonance signal; and an image processing unit that processes the image reconstructed by the imaging unit, wherein the image processing unit includes:

a noise reduction section that generates a second MR image in which noise and artifacts are reduced with respect to an original image acquired by the imaging unit;

a difference image generation section that generates a difference image by taking, for each pixel, a difference in signal intensity between the original image and the second MR image;

a weight calculation section that calculates, for each pixel, a corresponding weighting value by using the difference image; and a composite image generation section that generate the third MR image by using weights including for each pixel the corresponding weighting value to combine the original image and the second MR image through weighted averaging for each pixel and generates a third MR image, wherein the weight value applied for each pixel monotonically increases as a magnitude of the difference for the pixel in the difference image increases.

18. An image processing method of generating and presenting a third MR image by using a first MR image acquired by a magnetic resonance imaging apparatus and a second MR image obtained by performing processing of reducing noise and artifacts with respect to the first MR image, the image processing method comprising:

generating a difference image by taking, for each pixel, a difference in signal intensity between the first MR image and the second MR image;

calculating, for each pixel, a corresponding weighting value by using the difference image; and generating the third MR image by using weights including for each pixel the corresponding weighting value to combine the first MR image and the second MR image through weighted averaging for each pixel, the weight value applied for each pixel monotonically increasing as a magnitude of the difference for the pixel in the difference image increases.

19. The image processing method according to claim 18, wherein, in the calculation of the weighting value, a weight coefficient $\alpha$ with respect to a pixel value is calculated using the difference image, and the weight coefficient $\alpha$ is used as an exponent of a fixed weight W to decide on the weighting value for each pixel, which is denoted by $W^{\alpha}$.

20. The image processing method according to claim 19, wherein the fixed weight is set in advance according to a noise pattern included in the first MR image and the processing of reducing noise and artifacts.

* * * * *